US 6,737,554 B2

(12) United States Patent
Brandt et al.

(10) Patent No.: US 6,737,554 B2
(45) Date of Patent: May 18, 2004

(54) PROCESS FOR THE PRODUCTION OF A DINITRONAPHTHALENE ISOMER MIXTURE WITH A HIGH PROPORTION OF 1,5-DINITRONAPHTHALENE

(75) Inventors: Matthias Brandt, Düsseldorf (DE); Stephan Klein, Mettmann (DE); Gerhard Wegener, Mettmann (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/377,473

(22) Filed: Feb. 28, 2003

(65) Prior Publication Data

US 2003/0171627 A1 Sep. 11, 2003

(30) Foreign Application Priority Data

Mar. 5, 2002 (DE) .......................... 102 09 644

(51) Int. Cl.[7] ..................... C07C 205/00; C07C 209/00; C07C 249/00
(52) U.S. Cl. ..................... 568/931; 568/928; 568/930; 564/415; 560/359
(58) Field of Search ................ 568/931, 928, 568/930; 564/415; 560/359

(56) References Cited

U.S. PATENT DOCUMENTS

| 6,242,656 B1 | 6/2001 | Steinlein et al. ............ 568/930 |
| 6,420,616 B1 | 7/2002 | Gürtler et al. .............. 568/931 |

FOREIGN PATENT DOCUMENTS

| DE | 1 150 965 | 7/1963 |
| DE | 24 53 529 | 5/1976 |
| EP | 1 004 570 | 5/2000 |
| GB | 1 499 699 | 5/1976 |
| WO | 94/19310 | 9/1994 |
| WO | 96/36587 | 11/1996 |
| WO | 99/12886 | 3/1999 |

OTHER PUBLICATIONS

Bakhvalov et al , Chemical Abstract, document No. 123:116173, Nitration of naphthalene in the presence of zeolites (1995), 68 (1), 49–53.*
Houben–Weyl: Methoden der Organischen Chemie, 4th edition, vol. X/I (month unavailable) 1971, pp. 492–495, W. Seidenfaden u. D. Pawellek: "Aromatische Nitro–Verbindungen".
Database WPI, Section Ch, Week 199748, Derwent Publications Ltd., London, GB; AN 1997–524733, XP002244525 & RU 2 079 482 C (As Sibe Catalysis Inst), May 20, 1997 Zusammenfassung.
Database WPI, Section Ch, Week 199633, Derwent Publications Ltd., London, GB; AN 1996–329446, XP002244526 & JP 08 151353 A (Mitsui Toatsu Chem Inc), Jun. 11, 1996 Zusammenfassung.

* cited by examiner

Primary Examiner—J. Parsa
(74) Attorney, Agent, or Firm—Joseph C. Gil; Lyndanne M. Whalen

(57) ABSTRACT

The present invention relates to a process for the production of a dinitronaphthalene isomer mixture, in which naphthalene and/or 1-nitronaphthalene is reacted with nitric acid in the presence of a zeolite.

10 Claims, No Drawings

PROCESS FOR THE PRODUCTION OF A DINITRONAPHTHALENE ISOMER MIXTURE WITH A HIGH PROPORTION OF 1,5-DINITRONAPHTHALENE

BACKGROUND OF THE INVENTION

The invention relates to the production of a dinitronaphthalene isomer mixture with a high proportion of 1,5-dinitronaphthalene by the nitration of naphthalene, 1-nitronaphthalene or a crude nitronaphthalene mixture. 1,5-Dinitronaphthalene is a key compound for the production of 1,5-diaminonaphthalene. This is, among other things, useful as the starting compound for the production of 1,5-diisocyanatonaphthalene (trade name: Desmodur® 15). 1,5-Diisocyanatonaphthalene is used as an isocyanate component in polyurethane production.

The production of nitrated aromatics has been known for a long time (G. A. Olah et al., Nitration: Methods and Mechanisms, VCH, New York, 1989). For decades, corresponding nitroaromatics have been produced industrially by nitration with a mixture of sulfuric and nitric acids (so-called mixed or nitrating acid).

The mononitration of naphthalene yields an isomer mixture of 1-nitronaphthalene and 2-nitronaphthalene in a ratio of about 95:5. The direct dinitration of naphthalene, as well as the further nitration of 1-nitronaphthalene, produces 1,5-dinitronaphthalene and 1,8-dinitronaphthalene in a ratio of about 1:2 (Houben-Weyl: Methoden der Organischen Chemie, $4^{th}$ edition, 1971, vol. X/1, pp. 492–495). Other dinitronaphthalene isomers are also formed to a lesser extent (about 5%), e.g., 1,6- and 1,7-dinitronaphthalene. The unfavorable selectivity of the reactions means that, in the production of 1,5-dinitronaphthalene, a high and undesirable proportion of 1,8-dinitronaphthalene is preferentially formed.

In DE-OS-11 50 965, the production of dinitronaphthalenes starting from 1-nitronaphthalene is described. An increase in selectivity in favor of the desired 1,5-dinitronaphthalene is achieved by rapid and intensive mixing of the 1-nitronaphthalene dissolved in sulfuric acid with nitrating acid. A disadvantage of this process is the considerable quantity of sulfuric acid and its complex and cost-intensive reprocessing. In addition, considerable quantities of trinitrated products can be formed in this process. Such trinitrated products clearly reduce the yield of 1,5-dinitronaphthalene and are to be regarded as significant from a safety point of view, particularly with the adiabatic reaction described in the above prior art.

In WO-99/12886, a process for the production of a dinitronaphthalene isomer mixture with a high proportion of 1,5-dinitronaphthalene from nitronaphthalene is described. Here, the reaction of the nitronaphthalene with nitric acid takes place in a nitroalkane or sulfolane as solvent. In this process, however, product mixtures are obtained which still contain considerable proportions of the unreacted educt 1-nitronaphthalene. Another disadvantage lies in the low yields of 1,5-dinitronaphthalene, which is only contained in the product mixtures at a maximum of 28.3%.

WO-99/12887 also discloses a process in which nitronaphthalene is used to produce a dinitronaphthalene isomer mixture with a high proportion of 1,5-dinitronaphthalene. Here, the reaction of the nitronaphthalene with nitric acid takes place in the presence of a solid, perfluorinated, strongly acidic ion exchanger. In general, this process has the disadvantage that the resulting dinitronaphthalene isomer mixture has to be separated off from the catalyst by extraction with dioxane at 90° C. The dioxane then has to be removed by an additional distillation step. Another disadvantage of the process lies in the fact that, to achieve high conversions of the educt 1-nitronaphthalene, the nitric acid has to be added in a large excess (6 to 8 equivalents). The fact that the product mixtures with a relatively high proportion (>30%) of 1,5-dinitronaphthalene always contain still higher proportions of 1,8-dinitronaphthalene is also disadvantageous.

DE-OS-24 53 529 describes the production of dinitronaphthalenes by nitration of naphthalene or 1-nitronaphthalene with nitric acid in an organic solvent, e.g., dichloroethane, with the azeotropic removal of the water of reaction. This process yields dinitronaphthalene in high yields, but without influencing the isomer ratio.

WO-94/19310 describes nitration of aromatics on aluminum silicates partially doped with heavy metals, so-called "claycops", as solid catalysts. The nitration of naphthalene carried out by this process gives dinitronaphthalene in a high yield, but with an isomer ratio like that of classic nitrations with mixed acid.

In DE-A1-199 58 389, a process for the production of a dinitronaphthalene isomer mixture with an increased proportion of 1,5-dinitronaphthalene is described. In this process, naphthalene is reacted with nitric acid in the presence of at least one ionic liquid. However, these ionic liquids are very expensive and therefore unsuitable for use on an industrial scale. Another disadvantage of the process lies in the fact that very high excesses of nitric acid (8 to 22 equivalents per nitro group to be introduced) are used. Furthermore, the isomer proportion of the undesired 1,8-dinitronaphthalene, at 50 to 53%, is always clearly higher than that of 1,5-dinitronaphthalene (36.5 to 39%).

SUMMARY OF THE INVENTION

The object of the present invention is therefore to provide a simple and economic process for the production of a dinitronaphthalene isomer mixture by which a mixture of dinitronaphthalenes can be obtained in high yields and with a large proportion of 1,5-dinitronaphthalene.

It has been found that, when a zeolite is used as the catalyst in the nitration of naphthalene and/or 1-nitronaphthalene with nitric acid, a shift of the isomer ratio towards 1,5-dinitronaphthalene is possible.

DETAILED DESCRIPTION OF THE INVENTION

The invention provides a process for the production of a dinitronaphthalene isomer mixture, in which naphthalene and/or 1-nitronaphthalene is reacted with nitric acid in the presence of a zeolite.

The dinitronaphthalene isomer mixtures produced according to the invention contain a surprisingly high proportion of 1,5-dinitronaphthalene. The proportion of 1,5-dinitronaphthalene that can be achieved in the process is about 60 wt. %, based on the mixture of 1,5-dinitronaphthalene and 1,8-dinitronaphthalene. The content of other by-products, particularly other dinitronaphthalene isomers and products with a higher degree of nitration, is small.

In the process, naphthalene, pure 1-nitronaphthalene or else a crude nitronaphthalene mixture, as is obtained as a crude product in the mononitration of naphthalene, can be used as the starting product.

The process according to the invention is carried out in the presence of at least one zeolite. Mixtures of different zeolites can also be used.

In terms of their basic structure, zeolites are crystalline aluminosilicates, which are built up from a network of $SiO_4$ and $AlO_4$ tetrahedrons. The individual tetrahedrons are linked together with oxygen bridges at the vertices and form a spatial networks which is uniformly traversed by channels and cavities. As compensation for the negative charge of the lattice, exchangeable cations are included. Aluminum can be partially replaced by other elements, such as B, Ga, In, Fe, Cr, V, As, Sb or Be. In addition, silicon can be replaced by other tetravalent elements, such as Ge, Ti, Zr or Hf. The zeolites can additionally contain e.g. H, $NH_4$, Li, Na, K, Mg, Ca, Cu, Zn, rare earth metals, Ti, Zr, Sn(IV), Cr(III), Fe(II), Mn(II), Co or Ni as exchangeable cations.

Zeolites of the structure types MFI, MOR, BEA, FAU, MEL, EMT, MTW, LTL, MWW, RHO, FER or HEU (according to the structural classification from W. M. Meier, D. H. Olson, Ch. Baerlocher, Atlas of Zeolite Structure Types, 4$^{th}$ Edition, Elsevier, London, 1996) are preferably used in the acidic H$^+$ form. Individually, the zeolites H-beta, H—Y, H-mordenite and H-ZSM-5 are particularly suitable. Zeolites of the H—Y type are particularly preferably used.

Zeolites in the acidic H$^+$ form and their production are described in detail in the literature (R. Szostak, Handbook of Molecular Sieves, Van Nostrand Reinhold, New York, 1992).

The zeolite can be used without pre-treatment, or it can optionally also be pre-treated. The pre-treatment can take place, e.g., by calcination at a temperature of between 200 and 700° C., preferably 300 to 600° C. The calcination can be performed, e.g., over a period of 1 to 24 hours. After the calcination, the zeolite is cooled in air or, preferably, under an inert atmosphere, such as a nitrogen, helium or argon atmosphere, and then used for the nitration.

The zeolite can be used in the form of a powder, granule, particle, sphere, pellet or extrudate. Furthermore, the zeolite can be embedded into an inorganic matrix, which is preferably inert. Suitable inorganic matrix materials are, e.g., silicon dioxide, silicon carbide, aluminum oxide, synthetic porous materials or clay. In addition, the zeolite can also be applied on to a support structure, which is preferably inert. Suitable support structures are, e.g., ceramic monoliths, ceramic honeycomb structures, ceramic foams, ceramic structured packings, metal monoliths, metal honeycomb structures, metal foams, knitted wire meshes, metal supports with a cross-channel structure, metal structured packings and bag packings made of woven wire cloth.

When loss of activity occurs, the zeolite can be regenerated, e.g., by washing, acid treatment or calcination and then reused in the process according to the invention.

The nitric acid is preferably used as an aqueous solution. The concentration of the nitric acid used is preferably between 40 and 100 wt. %, more preferably between 50 and 100 wt. %, most preferably between 60 and 99 wt. %.

The nitric acid can be used in excess, in the stoichiometrically required quantity or in a less than stoichiometric amount. A nitric acid excess makes it easier to achieve a high naphthalene and/or 1-nitronaphthalene conversion; the unreacted nitric acid can be separated off and recycled into the process. A deficiency of nitric acid makes it easier to achieve a high to compete conversion of nitric acid; unreacted naphthalene and/or 1-nitronaphthalene can be separated off and recycled into the process.

Preferably, 0.2 to 40 moles, more preferably 0.4 to 20 moles of nitric acid per mole of naphthalene and/or preferably 0.1 to 20 moles, more preferably 0.2 to 10 moles of nitric acid per mole of 1-nitronaphthalene are used.

In one embodiment of the process of the present invention, the nitric acid is used in a mixture with sulfuric acid and/or phosphoric acid.

The optionally used sulfuric acid is preferably used as an aqueous solution. The concentration of the sulfuric acid is preferably between 85 and 100 wt. %, more preferably between 90 and 100 wt. %, and most preferably between 95 and 100 wt. %.

The optionally used phosphoric acid is preferably used as an aqueous solution. The concentration of the phosphoric acid is preferably between 50 and 99 wt. %, more preferably between 65 and 99 wt. %, and most preferably between 85 and 99 wt. %.

When a mixture of nitric acid and sulfuric acid and/or phosphoric acid is used, this mixture preferably includes 1 to 20 parts by weight of nitric acid and 1 part by weight of sulfuric acid and/or phosphoric acid, more preferably, 1 to 10 parts by weight of nitric acid and 1 part by weight of sulfuric acid and/or phosphoric acid, most preferably, 1 to 5 parts by weight of nitric acid and 1 part by weight of sulfuric acid and/or phosphoric acid.

The process of the present invention is preferably performed at temperatures of between 20 and 160° C., more preferably at temperatures of between 40 and 120° C. and most preferably at temperatures of between 50 and 100° C.

The process can be performed without solvents or in the presence of a solvent. The process is preferably performed in the presence of an organic solvent. Suitable solvents include any of the solvents that are stable under the conditions of the nitration such as hydrocarbons, halogenated hydrocarbons, carboxylic acids, nitroalkanes, nitroaromatics, sulfolane and dimethyl sulfoxide. Preferably, n-alkanes with 5 to 16 carbon atoms, cycloalkanes with 5 to 8 carbon atoms, ligroin, perfluorinated hydrocarbons, dichloromethane, chloroform, carbon tetrachloride, 1,2-dichloroethane, 1,2-dichloropropane, 1,2-dichlorobenzene, acetic acid, propionic acid, nitromethane, nitroethane, nitrobenzene, dinitrobenzene, sulfolane and dimethyl sulfoxide are used as the solvent, n-Hexane, n-heptane, cyclohexane, ligroin, dichloromethane, chloroform, 1,2-dichloroethane, 1,2-dichloropropane, acetic acid, nitromethane, nitroethane and sulfolane are particularly preferred solvents.

The quantity of organic solvent added, based on the quantity of naphthalene or nitronaphthalene used, is preferably between 10 and 10000 wt. %, more preferably between 50 and 5000 wt. %, most preferably between 100 and 5000 wt. %.

In the process of the present invention, mixtures of different solvents can also be used.

The process of the present invention can be performed continuously, partially continuously or discontinuously under reduced, normal or increased pressure. It is also possible to separate one or more components from the reaction mixture simultaneously with the reaction, e.g. by stripping, distillation or membrane separation processes. The process is preferably performed partially continuously under normal pressure. The process is particularly preferably carried out by metering the nitric acid into a mixture of naphthalene or nitronaphthalene, zeolite and optionally organic solvent at the desired reaction temperature, the zeolite preferably being used in a quantity of 1 to 1000 wt. %, more preferably 5 to 750 wt. %, based on the quantity of naphthalene or nitronaphthalene.

The process can be performed in a known manner in any of the various reactors that are suitable for solid-catalyzed liquid-phase reactions, e.g. stirred reactors, fixed bed reactors and fluidized bed reactors. A circulating operation is also possible. The process is preferably performed in stirred reactors.

The process is preferably performed by mixing naphthalene or 1-nitronaphthalene, the zeolite catalyst and optionally organic solvent together, heating to reaction temperature, and then adding the acid to be used all at once or over a longer period, continuously or in portions. In order to ensure that the reaction runs to completion, it is preferably performed with good, thorough mixing of the reaction mixture, e.g. by intensive stirring. The reaction period is usually between 5 minutes and 24 hours, preferably between 30 minutes and 18 hours. The reaction mixture can be worked up in a manner that is known to the person skilled in the art.

The zeolite catalyst can be separated from the reaction mixture on completion of the reaction by, e.g., filtration, sedimentation or centrifugation. If the zeolite is used as a fixed catalyst in a fixed bed reactor through which the remaining reaction mixture flows, no separate separation step is needed.

Unreacted naphthalene or 1-nitronaphthalene, excess nitric acid and optionally the solvent can be separated from the dinitronaphthalene isomer mixture formed by, e.g., phase separation, distillation or fractional crystallization, and recycled into the process.

The dinitronaphthalene isomer mixture can be separated into the isomeric dinitronaphthalenes, e.g., by fractional crystallization. These isomer separations, e.g., with dimethyl formamide or dichloroethane as solvents, are generally known (Houben-Weyl: Methoden der Organischen Chemie, 4$^{th}$ edition, 1971, vol. X/1, p. 494).

The invention also provides a process for the production of 1,5-diaminonaphthalene in which naphthalene and/or 1-nitronaphthalene is reacted with nitric acid in the presence of a zeolite and then the resulting 1,5-dinitronaphthalene is hydrogenated to form 1,5-diaminonaphthalene.

The invention also provides a process for the production of 1,5-diisocyanatonaphthalene in which naphthalene and/or 1-nitronaphthalene is reacted with nitric acid in the presence of a zeolite, the resulting 1,5-dinitronaphthalene is then hydrogenated to form 1,5-diaminonaphthalene and the resulting 1,5-diaminonaphthalene is phosgenated to form 1,5-diisocyanatonaphthalene.

The hydrogenation of 1,5-dinitronaphthalene to form 1,5-diaminonaphthalene and the phosgenation of 1,5-diaminonaphthalene to form 1,5-diisocyanatonaphthalene take place in the manner known from the prior art (Houben-Weyl: Methoden der Organischen Chemie, 4$^{th}$ edition, vol. XI/1, pp. 400–401 (1957) and Houben-Weyl: Methoden der Organischen Chemie, 4$^{th}$ edition, vol. E 4, pp. 741–748 (1983)).

Having thus described the invention, the following Examples are given as being illustrative thereof.

EXAMPLES

The zeolite catalysts used in the following examples were calcined for at least 3 hours at 500° C. prior to the reactions.

The composition of the resulting mixtures was analyzed by gas chromatography and quantified with the aid of an internal standard (n-hexadecane).

In all of the following examples, trinitronaphthalenes were not formed at all or, at the most, in very small quantities. No other by-products or derivative products were formed in any case.

Example 1

Nitration of 1-nitronaphthalene with Nitric Acid in the Presence of 1,2-dichloroethane and Zeolite H—Y 11.0 g of 1,2-dichloroethane, 0.6 g of 1-nitronaphthalene and 2.0 g of zeolite H—Y from PQ (powder, $SiO_2/Al_2O_3$= 60) were combined and heated to 73° C. Then, 0.60 g of 99 wt. % nitric acid were added all at once. The mixture was then stirred for 3 hours at 73° C. The work-up was performed by adding 10 ml of deionized water followed by extraction with 60 ml of dichloromethane. The result is listed in Table 1.

Example 2 (Comparative Example)

Nitration of 1-nitronaphthalene with Nitric Acid in the Presence of 1,2-dichloroethane 11.0 g of 1,2-dichloroethane and 0.6 g of 1-nitronaphthalene were combined and heated to 73° C. Then, 0.60 g of 99 wt. % nitric acid were added all at once. The mixture was then stirred for 3 hours at 73° C. The work-up was performed by adding 10 ml of deionized water followed by extraction with 60 ml of dichloromethane. The result is listed in Table 1.

Example 3

Nitration of 1-nitronaphthalene with Nitric Acid in the Presence of 1,2-dichloroethane and Zeolite H—Y 10.0 g of 1,2-dichloroethane, 0.60 g of 1-nitronaphthalene and 1.5 g of zeolite H—Y from PQ (powder, $SiO_2/Al_2O_3$= 60) were combined and heated to 80° C. Then, 0.30 g of 99 wt. % nitric acid were added all at once. The mixture was then stirred for 22 hours at 80° C. The work-up was performed by adding 10 ml of deionized water followed by extraction with 60 ml of dichloromethane. The result is listed in Table 1.

Example 4

Nitration of 1-nitronaphthalene with Nitric Acid in the Presence of 1,2-dichloroethane and Zeolite H—Y 10.0 g of 1,2-dichloroethane, 0.30 g of 1-nitronaphthalene and 1.5 g of zeolite H—Y from PQ (powder, $SiO_2/Al_2O_3$= 60) were combined and heated to 80° C. Then, 0.30 g of 99 wt. % nitric acid were added all at once. The mixture was then stirred for 50 minutes at 80° C. The work-up was performed by adding 10 ml of deionized water followed by extraction with 60 ml of dichloromethane. The result is listed in Table 1.

Example 5

Nitration of 1-nitronaphthalene with Nitric Acid in the Presence of 1,2-dichloroethane and Zeolite H—Y 10.0 g of 1,2-dichloroethane, 0.50 g of 1-nitronaphthalene and 1.5 g of zeolite H—Y from PQ (powder, $SiO_2/Al_2O_3$= 30) were combined and heated to 70° C. Then, 0.60 g of 99 wt. % nitric acid were added in stages within 30 minutes. The mixture was then stirred for 210 minutes at 70° C. The work-up was performed by adding 10 ml of deionized water followed by extraction with 60 ml of dichloromethane. The result is listed in Table 1.

Example 6 (Comparative Example)

Nitration of 1-nitronaphthalene with Nitric Acid in the Presence of 1,2-dichloroethane 10.0 g of 1,2-dichloroethane and 0.50 g of 1-nitronaphthalene were combined and heated to 70° C. Then, 0.60 g of 99 wt. % nitric acid were added in stages within 30 minutes. The mixture was then stirred for 210 minutes at 70° C. The work-up was performed by adding 10 ml of deionized water followed by extraction with 60 ml of dichloromethane. The result is listed in Table 1.

Example 7
Nitration of 1-nitronaphthalene with Nitric Acid in the Presence of Chloroform and Zeolite H—Y 10.0 g of chloroform, 0.40 g of 1-nitronaphthalene and 1.5 g of zeolite H—Y from PQ (powder, $SiO_2/Al_2O_3$=30) were combined and heated to 61° C. Then, 0.90 g of 99 wt. % nitric acid were added in stages within 50 minutes. The mixture was then stirred for 190 minutes at 61° C. The work-up was performed by adding 10 ml of deionized water followed by extraction with 60 ml of dichloromethane. The result is listed in Table 1.

Example 8 (Comparative Example)
Nitration of 1-nitronaphthalene with Nitric Acid in the Presence of Chloroform 10.0 g of chloroform and 0.40 g of 1-nitronaphthalene were combined and heated to 61° C. Then, 0.90 g of 99 wt. % nitric acid were added in stages within 50 minutes. The mixture was then stirred for 190 minutes at 61° C. The work-up was performed by adding 10 ml of deionized water followed by extraction with 60 ml of dichloromethane. The result is listed in Table 1.

Example 9
Nitration of 1-nitronaphthalene with Nitric Acid in the Presence of n-heptane and Zeolite H—Y 6.5 g of n-heptane, 0.50 g of 1-nitronaphthalene and 1.5 g of zeolite H—Y from PQ (powder, $SiO_2/Al_2O_3$=12) were combined and heated to 60° C. Then, 0.45 g of 99 wt. % nitric acid were added in stages within 20 minutes. The mixture was then stirred for 160 minutes at 60° C. The work-up was performed by adding 10 ml of deionized water followed by extraction with 60 ml of dichloromethane. The result is listed in Table 1.

Example 10
Nitration of 1-nitronaphthalene with Nitric Acid in the Presence of 1,2-dichloroethane and Sulfolane and Zeolite H—Y 10.0 g of 1,2-dichloroethane, 1.5 g of sulfolane, 0.60 g of 1-nitronaphthalene and 1.5 g of zeolite H—Y from PQ (powder, $SiO_2/Al_2O_3$=30) were combined and heated to 80° C. Then, 0.60 g of 99 wt. % nitric acid were added in stages within 30 minutes. The mixture was then stirred for 180 minutes at 80° C. The work-up was performed by adding 10 ml of deionized water followed by extraction with 60 ml of dichloromethane. The result is listed in Table 1.

Example 11
Nitration of 1-nitronaphthalene with Nitric Acid in the Presence of 1,2-dichloroethane and Zeolite H—Y 10.0 g of 1,2-dichloroethane, 0.20 g of 1-nitronaphthalene and 1.5 g of zeolite H—Y from PQ (powder, $SiO_2/Al_2O_3$=30) were combined and heated to 83° C. Then, 0.15 g of 99 wt. % nitric acid were added all at once. The mixture was then stirred for 1 hour at 83° C. The work-up was performed by adding 10 ml of deionized water followed by extraction with 60 ml of dichloromethane. The result is listed in Table 1.

Example 12
Nitration of 1-nitronaphthalene with Nitric Acid in the Presence of 1,2-dichloroethane and Zeolite H—Y 10.0 g of 1,2-dichloroethane, 0.20 g of 1-nitronaphthalene and 1.5 g of zeolite H—Y from PQ (powder, $SiO_2/Al_2O_3$=30) were combined and heated to 50° C. Then, 0.23 g of 99 wt. % nitric acid were added all at once. The mixture was then stirred for 4 hours at 50° C. The work-up was performed by adding 10 ml of deionized water followed by extraction with 60 ml of dichloromethane. The result is listed in Table 1.

Example 13
Nitration of 1-nitronaphthalene with Nitric Acid in the Presence of 1,2-dichloroethane and Zeolite H—Y 10.0 g of 1,2-dichloroethane, 0.30 g of 1-nitronaphthalene and 1.5 g of zeolite H—Y from PQ (powder, $SiO_2/Al_2O_3$=60) were combined and heated to 80° C. Then, 0.30 g of 99 wt. % nitric acid were added all at once. The mixture was then stirred for 20 minutes at 80° C. The work-up was performed by adding 10 ml of deionized water followed by extraction with 60 ml of dichloromethane. The result is listed in Table 1.

Example 14
Nitration of 1-nitronaphthalene with Nitric Acid in the Presence of Nitromethane and Zeolite H—Y 10.0 g of nitromethane, 0.60 g of 1-nitronaphthalene and 1.5 g of zeolite H—Y from PQ (powder, $SiO_2/Al_2O_3$=30) were combined and heated to 78° C. Then, 0.60 g of 99 wt. % nitric acid were added in stages within 30 minutes. The mixture was then stirred for 210 minutes at 78° C. The work-up was performed by adding 10 ml of deionized water followed by extraction with 60 ml of dichloromethane. The result is listed in Table 1.

Example 15 (Comparative Example)
Nitration of 1-nitronaphthalene with Nitric Acid in the Presence of Nitromethane 10.0 g of nitromethane and 0.60 g of 1-nitronaphthalene were combined and heated to 78° C. Then, 0.90 g of 99 wt. % nitric acid were added in stages within 50 minutes. The mixture was then stirred for 190 minutes at 78° C. The work-up was performed by adding 10 ml of deionized water followed by extraction with 60 ml of dichloromethane. The result is listed in Table 1.

Example 16
Nitration of 1-nitronaphthalene with Nitric Acid in the Presence of Nitromethane and 1,2-dichloromethane and Zeolite H—Y 5.0 g of nitromethane, 5.0 g of 1,2-dichloroethane, 0.60 g of 1-nitronaphthalene and 1.5 g of zeolite H—Y from PQ (powder, $SiO_2/Al_2O_3$=30) were combined and heated to 78° C. Then, 0.60 g of 99 wt. % nitric acid were added in stages within 30 minutes. The mixture was then stirred for 210 minutes at 78° C. The work-up was performed by adding 10 ml of deionized water followed by extraction with 60 ml of dichloromethane. The result is listed in Table 1.

Example 17
Nitration of 1-nitronaphthalene with Nitric Acid in the Presence of Nitromethane and Zeolite H—Y 10.0 g of nitromethane, 0.80 g of 1-nitronaphthalene and 0.4 g of zeolite H—Y from PQ (powder, $SiO_2/Al_2O_3$=30) were combined and heated to 80° C. Then, 1.20 g of 99 wt. % nitric acid were added in stages within 70 minutes. The mixture was then stirred for 170 minutes at 80° C. The work-up was performed by adding 10 ml of deionized water followed by extraction with 60 ml of dichloromethane. The result is listed in Table 1.

Example 18
Nitration of 1-nitronaphthalene with Nitric Acid in the Presence of Nitroethane and Zeolite H—Y 10.0 g of nitroethane, 0.50 g of 1-nitronaphthalene and 1.5 g of zeolite H—Y from PQ (powder, $SiO_2/Al_2O_3=80$) were combined and heated to 78° C. Then, 0.75 g of 99 wt. % nitric acid were added in stages within 40 minutes. The mixture was then stirred for 200 minutes at 78° C. The work-up was performed by adding 10 ml of deionized water followed by extraction with 60 ml of dichloromethane. The result is listed in Table 1.

Example 19 (Comparative Example)
Nitration of 1-nitronaphthalene with Nitric Acid in the Presence of Nitroethane 10.0 g of nitroethane and 0.50 g of 1-nitronaphthalene were combined and heated to 78° C. Then, 0.75 g of 99 wt. % nitric acid were added in stages within 40 minutes. The mixture was then stirred for 200 minutes at 78° C. The work-up was performed by adding 10 ml of deionized water followed by extraction with 60 ml of dichloromethane. The result is listed in Table 1.

TABLE 1

| Example | $HNO_3$/1-NN (mol/mol) | C (1-NN) (%) | R (1,5-DNN) (%) | R (1,8-DNN) (%) | 1,5-DNN/1,8-DNN (mol/mol) | Y (1,5-DNN) (%) |
|---|---|---|---|---|---|---|
| 1 | 2.7 | 74.5 | 44.2 | 44.4 | 0.99 | 32.7 |
| 2 (comp.) | 2.7 | 38.8 | 25.5 | 70.7 | 0.36 | 9.9 |
| 3 | 1.35 | 86.5 | 44.1 | 45.2 | 0.98 | 38.1 |
| 4 | 2.7 | 98.5 | 46.2 | 44.3 | 1.04 | 45.5 |
| 5 | 3.3 | 92.5 | 45.2 | 43.9 | 1.03 | 41.7 |
| 6 (comp.) | 3.3 | 77.6 | 25.8 | 70.6 | 0.37 | 20.0 |
| 7 | 6.1 | 96.0 | 40.5 | 49.7 | 0.82 | 38.7 |
| 8 (comp.) | 6.1 | 93.3 | 26.3 | 70.7 | 0.37 | 24.5 |
| 9 | 2.4 | 65.4 | 44.1 | 44.9 | 0.98 | 28.5 |
| 10 | 2.7 | 58.2 | 44.9 | 47.7 | 0.95 | 26.2 |
| 11 | 2.0 | 100 | 48.6 | 41.2 | 1.18 | 48.6 |
| 12 | 3.1 | 100 | 50.3 | 40.8 | 1.23 | 50.3 |
| 13 | 2.7 | 78.0 | 48.7 | 41.8 | 1.16 | 37.9 |
| 14 | 2.7 | 99.0 | 57.9 | 34.8 | 1.66 | 57.3 |
| 15 (comp.) | 4.1 | 83.3 | 36.7 | 57.2 | 0.64 | 30.6 |
| 16 | 2.7 | 91.6 | 54.0 | 38.1 | 1.42 | 49.5 |
| 17 | 4.1 | 99.2 | 48.6 | 44.0 | 1.11 | 48.2 |
| 18 | 4.1 | 100 | 50.4 | 44.0 | 1.14 | 50.4 |
| 19 (comp.) | 4.1 | 73.6 | 35.4 | 59.3 | 0.60 | 26.1 |

(comp.): comparative example
1-NN: 1-nitronaphthalene
1,5-DNN: 1,5-dinitronaphthalene
1,8-DNN: 1,8-dinitronaphthalene
C: conversion
R: regioselectivity = isomer proportion
Y: yield

Example 20
Nitration of Naphthalene with Nitric Acid in the Presence of 1,2-dichloroethane and Zeolite H—Y 10.0 g of 1,2-dichloroethane, 0.44 g of naphthalene and 1.5 g of zeolite H—Y from Degussa (extrudate ground into powder, $SiO_2/Al_2O_3=55$) were combined and heated to 80° C. Then, 0.90 g of 99 wt. % nitric acid were added in stages within 40 minutes. The mixture was then stirred for 200 minutes at 80° C. The work-up was performed by adding 10 ml of deionized water followed by extraction with 60 ml of dichloromethane.

Results:
  Conversion of naphthalene: 100%
  Yield of 1-nitronaphthalene: 1.0%
  Regioselectivity to 1,5-dinitronaphthalene: 38.3%
  Regioselectivity to 1,8-dinitronaphthalene: 46.8%
  Molar ratio of 1,5-/1,8-dinitronaphthalene: 0.82

Example 21 (Comparative Example)
Nitration of Naphthalene with Nitric Acid in the Presence of 1,2-dichloroethane 10.0 g of 1,2-dichloroethane and 0.44 g of naphthalene were combined and heated to 80° C. Then, 0.90 g of 99 wt. % nitric acid were added in stages within 20 minutes. The mixture was then stirred for 220 minutes at 80° C. The work-up was performed by adding 10 ml of deionized water followed by extraction with 60 ml of dichloromethane.

Results:
  Conversion of naphthalene: 100%
  Yield of 1-nitronaphthalene: 62.2%
  Regioselectivity to 1,5-dinitronaphthalene: 25.2%
  Regioselectivity to 1,8-dinitronaphthalene: 65.7%
  Molar ratio of 1,5-/1,8-dinitronaphthalene: 0.38

Example 22
Nitration of 1-nitronaphthalene with Nitric Acid in the Presence of Sulfolane and Zeolite H—Y 302 g of sulfolane, 15 g of 1-nitronaphthalene and 30 g of zeolite H—Y from Degussa (extrudate ground into powder, $SiO_2/Al_2O_3=23$) were combined and heated to 80° C. Then, 44 g of 99 wt. % nitric acid were added within 30 minutes. The mixture was then stirred for 2 hours at 80° C. The work-up was performed by adding deionized water followed by extraction with dichloromethane.

Results:
  Conversion of 1-nitronaphthalene: 25.6%
  Regioselectivity to 1,5-dinitronaphthalene: 55.5%
  Regioselectivity to 1,8-dinitronaphthalene: 37.3%
  Molar ratio of 1,5-/1,8-dinitronaphthalene: 1.49
  Yield of 1,5-dinitronaphthalene: 14.2%

Example 23
Nitration of 1-nitronaphthalene with Nitric Acid in the Presence of Sulfolane and Zeolite H—Y 302 g of sulfolane, 15 g of 1-nitronaphthalene and 30 g of zeolite H—Y from PQ (powder, $SiO_2/Al_2O_3=60$) were combined and heated to 80° C. Then, 52 g of 99 wt. % nitric acid were added within 30 minutes. The mixture was then stirred for 2 hours at 80° C. The work-up was performed by adding deionized water followed by extraction with dichloromethane.

Results:
  Conversion of 1-nitronaphthalene: 53.3%
  Regioselectivity to 1,5-dinitronaphthalene: 51.7%
  Regioselectivity to 1,8-dinitronaphthalene: 41.3%
  Molar ratio of 1,5-/1,8-dinitronaphthalene: 1.25
  Yield of 1,5-dinitronaphthalene: 27.6%

Example 24 (Comparative Example)
Nitration of 1-nitronaphthalene with Nitric Acid in the Presence of Sulfolane 302 g of sulfolane and 25 g of 1-nitronaphthalene were combined and heated to 80° C. Then, 55 g of 99 wt. % nitric acid were added within 40 minutes. The mixture was then stirred for 2 hours at 80° C. The work-up was performed by adding deionized water followed by extraction with dichloromethane.

Results:
- Conversion of 1-nitronaphthalene: 16.3%
- Regioselectivity to 1,5-dinitronaphthalene: 36.0%
- Regioselectivity to 1,8-dinitronaphthalene: 53.5%
- Molar ratio of 1,5-/1,8-dinitronaphthalene: 0.67
- Yield of 1,5-dinitronaphthalene: 5.8%

Example 25

Nitration of 1-nitronaphthalene with Nitric Acid in the Presence of Nitromethane and Zeolite H—Y 300 g of nitromethane, 18 g of 1-nitronaphthalene and 12 g of zeolite H—Y from PQ (powder, $SiO_2/Al_2O_3=30$) were combined and heated to 80° C. Then, 26 g of 99 wt. % nitric acid were added within 60 minutes. The mixture was then stirred for 210 minutes at 80° C. After this period the reaction mixture was separated from the zeolite and this was extracted twice more with 500 ml of 1,2-dichloroethane each time and twice with 500 ml of dichloromethane each time (30 minutes at room temperature each time). The product phases were worked up and the composition of the solid crude product obtained was determined by gas chromatography and quantified with the aid of an internal standard (n-hexadecane):

- Isomer proportion of 1,5-dinitronaphthalene: 50.2%
- Isomer proportion of 1,8-dinitronaphthalene: 42.6%
- Ratio of 1,5-/1,8-dinitronaphthalene: 1.18

The crude product was a dinitronaphthalene isomer mixture containing no 1-nitronaphthalene, no trinitronaphthalenes and no other by-products. 19.2 g of this crude product were obtained. This corresponds to a 1,5-dinitronaphthalene yield of 42.5%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a dinitronaphthalene isomer mixture having an increased proportion of 1,5-dinitronaphthalene isomer comprising reacting naphthalene and/or 1-nitronaphthalene with nitric acid in the presence of a zeolite.

2. The process of claim 1 in which the reaction is performed in the presence of at least one organic solvent.

3. The process of claim 2 in which n-hexane, n-heptane, cyclohexane, ligroin, dichloromethane, chloroform, 1,2-dichloroethane, 1,2-dichloro-propane, acetic acid, nitromethane, nitroethane or sulfolane is used as the organic solvent.

4. The process of claim 1 in which the concentration of the nitric acid used is between 40 and 100 wt. %.

5. The process of claim 1 in which from 0.2 to 40 moles of nitric acid per mole of naphthalene and/or 0.1 to 20 moles of nitric acid per mole of 1-nitronaphthalene are used.

6. The process of claim 1 in which the nitric acid is used in a mixture with sulfuric acid and/or phosphoric acid.

7. The process of claim 1 in which the zeolite is a MFI, MOR, BEA, FAU, MEL, EMT, MTW, LTL, MWW, RHO, FER or HEU structure type and is used in the acidic $H^+$ form.

8. The process of claim 1 in which the zeolite is a H—Y, H-beta, H-mordenite or H-ZSM-5 type.

9. A process for the production of 1,5-diaminonaphthalene comprising
   a) reacting naphthalene and/or 1-nitronaphthalene with nitric acid in the presence of a zeolite to form an isomeric mixture having an increased proportion of 1,5-dinitronaphthalene, and
   b) hydrogenating the reaction product of a) to form 1,5-diaminonaphthalene.

10. A process for the production of 1,5-diisocyanatonaphthalene comprising
    a) reacting naphthalene and/or 1-nitronaphthalene with nitric acid in the presence of a zeolite to form an isomeric mixture having an increased proportion of 1,5-dinitronaphthalene,
    b) hydrogenating the 1,5-dinitronaphthalene to form 1,5-diaminonaphthalene, and
    c) phosgenating the 1,5-diaminonaphthalene to form 1,5-diisocyanatonaphthalene.

* * * * *